United States Patent
John (10) Patent No.: US 6,170,342 B1
(45) Date of Patent: Jan. 9, 2001

(54) SPIRAL SAMPLER

(75) Inventor: Walter John, Walnut Creek, CA (US)

(73) Assignees: Particle Science, Walnut Creek; Aerosol Dynamics Inc., Berkely, both of CA (US)

(*) Notice: Under 35 U.S.C. 154(b), the term of this patent shall be extended for 0 days.

(21) Appl. No.: 09/020,788

(22) Filed: Feb. 9, 1998

Related U.S. Application Data (60) Provisional application No. 60/046,975, filed on May 19, 1997.

(51) Int. Cl.[7] .................................................. G01N 1/00
(52) U.S. Cl. ............................................................ 73/863.21
(58) Field of Search ........................... 73/863.21, 863.41, 73/863.43, 864.33, 864.73, 28.04, 31.07

(56) References Cited

U.S. PATENT DOCUMENTS

| | | |
|---|---|---|
| 2,386,282 | 10/1945 | Watson et al. . |
| 3,070,990 | 1/1963 | Krinov . |
| 3,074,627 | 1/1963 | Goetz . |
| 3,458,974 | 8/1969 | Orr, Jr. et al. . |
| 3,693,791 | 9/1972 | Beck . |
| 3,807,218 | 4/1974 | Carson et al. . |
| 3,823,602 * | 7/1974 | Anderson ............................. 73/28.04 |
| 3,966,439 | 6/1976 | Vennos . |
| 4,133,202 | 1/1979 | Marple . |
| 4,138,880 * | 2/1979 | Cohen et al. ........................ 73/31.07 |
| 4,279,156 | 7/1981 | Bell . |
| 4,350,507 | 9/1982 | Greenough et al. . |
| 4,400,982 | 8/1983 | Bell . |
| 4,452,068 | 6/1984 | Loo . |
| 4,461,183 | 7/1984 | Wedding . |
| 4,463,595 | 8/1984 | Yeh et al. . |
| 4,488,887 * | 12/1984 | Angel et al. ........................ 73/863.22 |
| 4,670,135 | 6/1987 | Marple et al. . |

(List continued on next page.)

OTHER PUBLICATIONS

Hatch, Theodore and W. C. L. Hemeon, Influence of Particle Size in Dust Exposure, J. Ind. Hyg. Toxicol., vol. 30, pp. 172–180, May 1948.

Brown, J.H., et al., Influence of Particle Size upon the Retention of Particulate Matter in the Human Lung, Amer. J. of Public Health, vol. 40, pp. 450–458, Apr. 1950.

Yaffe, Charles D., et al., The Spiral Sampler—A New Tool for Studying Particulate Matter, Ind. Hyg. & Occ. Med., vol. 5, pp. 62–70, 1952.

Davies, C.N., Dust Sampling and Lung Disease, Brit. J. Industr. Med., vol. 9, pp. 120–126, 1952.

Marple, Virgil A., Simulation of Respirable Penetration Characteristics By Inertial Impaction, J. Aerosol Sci., vol. 9, pp. 125–134, 1978.

Marple, Virgil A., et al., Personal Sampling Impactor with Respirable Aerosol Penetration Characteristics, Am. Ind. Hyg. Assoc. J., vol. 44, pp. 916–922, Dec. 1983.

Macher, J.M., et al., Personal Air Samplers for Measuring Occupational Exposures to Biological Hazards, Am. Ind. Hyg. Assoc. J., vol. 45, pp. 76–83, Feb. 1984.

*Primary Examiner*—Robert Raevis
(74) *Attorney, Agent, or Firm*—James Creighton Wray; Meera P. Narasimhan (57) ABSTRACT

The SPIRAL SAMPLER is a sampler for airborne particles. The spiral groove in the sampler allows for sticky or liquid particles as well as solid or bouncy particles of any given aerodynamic diameter to be sampled with the same efficiency. The SPIRAL SAMPLER does not require any oil or grease, which may become dislodged during operation and contaminate the particle deposit. By varying the dimensions of the inlet tube and the spiral groove, as well as the number of turns of the spiral, samplers may be made for sampling at any desired flow rate and with chosen particle size cutoffs. The SPIRAL SAMPLER may be scaled to any size, from personal to an area sampler. For sampling in areas with high loadings of large particles, a particle trap may be used to effectively and compactly separate oversized particles which would adversely affect the sampler operator.

40 Claims, 4 Drawing Sheets

U.S. PATENT DOCUMENTS

| | | |
|---|---|---|
| 4,737,171 | 4/1988 | Courbon . |
| 5,040,424 | 8/1991 | Marple et al. . |
| 5,332,550 | 7/1994 | Booker . |
| 5,355,719 | 10/1994 | Kohsaka et al. . |
| 5,412,975 | 5/1995 | Raabe et al. . |
| 5,596,136 * | 1/1997 | Flagan et al. ........................ 73/28.04 |
| 5,942,440 * | 4/1997 | Dooley et al. .................... 73/864.73 |

* cited by examiner

SPIRAL SAMPLER

This application claims the benefit of U.S. Provisional Application No. 60/046,975, filed May 19, 1997.

BACKGROUND OF THE INVENTION

The present invention is used for sampling particles, particularly airborne particles (aerosols). There are many reasons for the sampling of aerosols including the assessment of air pollution in the atmosphere, indoors and in workplaces. Because the effects of aerosols on human health, materials, visibility, etc. depend on particle size, it is necessary to sample the aerosols with particle size selection in order to properly assess the effects. For example, inhaled particles beyond a certain size will not reach the pulmonary region of the human lung.

For some applications, public agencies and other organizations have adopted size-selective sampling criteria specifying sampling efficiency vs particle size. Apparatus for size-selective particle sampling generally consists of an inlet followed by a means to remove unwanted large particles from the airstream. The remaining airborne particles may then be collected on a filter or detected by an electronic sensing device.

A principal deficiency in prior samplers is excess penetration of solid particles compared to liquid particles because of particle bounce from collection surfaces. Some prior samplers attempt to minimize the problem by greasing or oiling collection surfaces. However, the grease loses its effectiveness as it becomes coated with particles. There is also the danger of the grease or oil migrating to the filter, and contaminating the particle deposit. The greased or oiled surfaces necessitate frequent maintenance that, if not done timely and properly, results in poor sampling performance. Cyclones are an exception in that they are free of particle bounce problems. However, their geometry is inconvenient for many applications.

SUMMARY OF THE INVENTION

The invention, named a SPIRAL SAMPLER, is a sampler for airborne particles. A unique feature is a curved channel or spiral groove in the groove plate. Air containing suspended particles enters the inlet tube attached at 90° to the front plate. Air leaving the inlet tube turns sharply by 90° and enters the curved channel or spiral groove, such as, a channel in the groove plate.

The front plate covers the channel, and a gasket between the plates provides a vacuum seal. At the end of the spiral groove, the air turns another 90° and exits the groove plate. The air then passes through a filter held by the filter back plate, which is attached to the groove plate. Particles are deposited on the filter, which may be removed for analysis of particle mass and/or chemical composition.

Another preferred alternative is to replace the filter back plate with the APS (Aerodynamic Particle Sizer) back plate to conduct the airborne particles to the entrance of an electronic particle detector, an existing device not part of this invention. The particle detector may count and size the particles in real time. A number of other existing particle detectors may be used.

The present invention may be used as a particle size selector at the inlet of other devices as well. Air is drawn through the sampler by a vacuum pump attached to the outlet tube when the filter back plate is used or by the vacuum pump in the electronic particle detector when the APS back plate is used.

The inlet tube produces a jet of air that impinges on the surface of the groove plate. That causes particles that are considerably larger than those of interest to impact on the surface. Some are retained on the surface, others may bounce and enter the spiral groove along with the smaller, suspended particles.

The air flow in the spiral groove follows the curve of the groove, resulting in a centrifugal force toward the outside wall. That further results in the formation of two counter-rotating eddies. Thus, the overall air motion consists of two counter-rotating spirals within the spiral groove. The secondary flows have a major effect in augmenting particle deposition on the outer walls of the spiral groove.

For given dimensions of the spiral groove and a given air flow rate, the percentage of particles penetrating to the filter (i.e., leaving the groove plate without depositing) depends on the particle's aerodynamic diameter. The graph of percentage of particles penetrating vs. particle aerodynamic diameter will have a 50% efficiency (the cutpoint) and the curve will have a characteristic shape.

Three preferable prototype SPIRAL SAMPLERS have been constructed and tested in the aerosol laboratory. One sampler, with the 4 $\mu$m groove plate, when operated at a flow rate of 2.8 liters/minute, has been shown to sample particles with a penetration curve closely following that of the ACGIH respirable mass criteria (American Conference of Governmental Industrial Hygienists).

A prototype with the 2.5 $\mu$m groove plate, when operated at a flow rate of 2.4 liters/minute, has been shown to sample particles with a penetration curve closely following that of the 1997 PM-2.5 Federal Reference Method for the sampling of ambient airborne particles by the U.S. Environmental Protection Agency.

The utility of the sampler is in its ability to sample particles according to a desired penetration curve. An additional important requirement is that sticky or liquid particles and solid, or bouncy particles of the same aerodynamic diameter be sampled with the same efficiency. Testing of the prototype with particles of oleic acid, a liquid, and particles of latex, a solid, verify that the SPIRAL SAMPLER satisfies that requirement.

The present invention causes the particles to deposit relatively gently and at grazing angles on the walls, which inhibits solid particle bounce. In addition, the particle deposition is distributed over a large area.

Some existing particle samplers use oil or grease on the deposition surfaces to reduce particle bounce. However, that has the disadvantages that oil or grease may be dislodged and deposited on the filter. Also, vapors from the oil or grease may contaminate the particle deposit on the filter.

The present SPIRAL SAMPLER is operated without oil or grease on the surfaces, thus eliminating the above disadvantages. A further advantage of the SPIRAL SAMPLER is the relatively small pressure drop because of the absence of any small orifices as in many other types of particle samplers.

By varying the dimensions of the inlet tube and the spiral groove as well as the number of turns of the spiral, SPIRAL SAMPLERs may be designed for sampling at any desired flow rate and with chosen particle size cutoffs. Preferred SPIRAL SAMPLERs may be made in a physically small version, such as the prototype, suitable for wearing on the person in combination with a small, battery-powered pump. The small, low flow rate version may also be used as a portable area sampler. Larger versions may be operated as area samplers with electrically-powered pumps.

The SPIRAL SAMPLER is a sampler for airborne particles. The curved channel or spiral groove removes large particles from the air stream before it reaches the filter or the APS, depending on which back is used, as shown in the drawings.

Three different preferred groove plates are specified, with different channel/groove widths, but with the same groove depth. The spiral grooves are formed from arcs of circles with various radii. The critical tolerances are on the depth and width of the spiral grooves. Note that the absolute radii are not as important as the width of the groove. Also, the transitions between different radii should be smooth.

The other critical tolerances are on the O-ring groove and the beveled surfaces of the filter back or APS back. Note that the O-ring groove is not conventional. The O-ring fits the inner diameter of the O-ring groove. On the outside, the O-ring seals against the beveled edge on the opposing surface, i.e., the filter or APS back. That configuration seals against the filter and also against the outside. For that configuration to be effective, the dimensions must be accurate.

In preferred embodiments, all parts are of suitable material, including but not limited to, aluminum or conducting plastic, and preferred materials for the O-ring and the gasket include rubber.

The SPIRAL SAMPLER is an instrument to be used in the general field of air pollution, in particular, the sampling of airborne particulate matter for the measurement of the concentration and/or the determination of the chemical composition of the particles. Such airborne particles may be located in outside air where concentration measurements are needed by governmental agencies seeking to protect public health. Airborne particles are also found indoors and in workplaces, where industrial hygienists assess and control health hazards.

The SPIRAL SAMPLER is compact since the preferred spiral groove plate is of the same circular shape as the filter holder.

The invention provides a sample of airborne particles according to a prescribed sampling convention such as the ACGIH Respirable Particle Mass or the U.S. Environmental Protection Agency's PM-2.5. The sampler is capable of collecting particles of any given aerodynamic diameter with the same efficiency, whether they are sticky or bouncy, and without having greased or oiled surfaces. The sampler is more compact than the most widely used current personal samplers. It may be mass-produced economically because of the relatively simple configuration. Because the assessment of airborne particle pollution is necessary everywhere: in the outdoors, in workplaces and in indoor areas, the potential market is very large.

The new size-selective aerosol particle sampler samples particles below a given particle aerodynamic range. The size selection is made by the present particle size selection device.

Particles enter the inlet opening and turn 90° thereby causing the largest particles to impact on the back wall. The remaining particles travel around in the curved channel or spiral groove. Centrifugal force causes larger particles to deposit on the outer wall of the groove. Smaller particles remain airborne and exit to a filter collector or a particle sensor. The 50% particle size cut-off and the shape of the cut-off curve are determined by the airflow rate, the size of the groove and the length or number of turns of the groove.

A particle trap preferably provides a removal mechanism for high loadings of large particles. The trap may be a virtual impaction stage, removing particles larger than a given size.

A conceptual design for a filter sampler is shown in the filter sampler schematic drawing. The front plate may be removed to clean the spiral groove and particle trap. The front plate is backed by a flat gasket to seal the spiral groove. In the filter sampler, the back plate may be removed to change the filter. A particle sensor may replace the filter. In both cases, the new SPIRAL SAMPLER effectively and compactly separates the oversized particles that otherwise would adversely affect the sampling.

The new sampler provides aerodynamic particle size selection. Particle size cut-off may be selected over a wide inertial size range. The new sampler may be scaled to any size from a personal to an area sampler. The flat geometry enables the design of a badge-type personal sampler. It may be used with a pocket pump or a belt-type pump. The design is tolerant of high loadings and coarse particles. The new sampler is simple and low cost for manufacturing. It may be replicated by automated mills or by plastic molding. The new sampler may be designed for low or high flow rates.

DETAILED DESCRIPTION OF THE PREFERRED EMBODIMENTS

Figure 1:
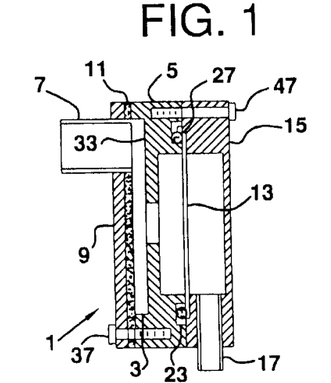
FIG. 1 is a side cross-sectional elevation of a SPIRAL SAMPLER with a filter backing plate.
Figure 2:
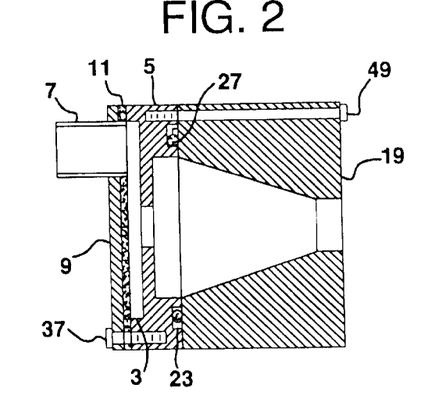
FIG. 2 is a side cross-sectional elevation of a SPIRAL SAMPLER with an APS sensor backing plate.
Figure 14:
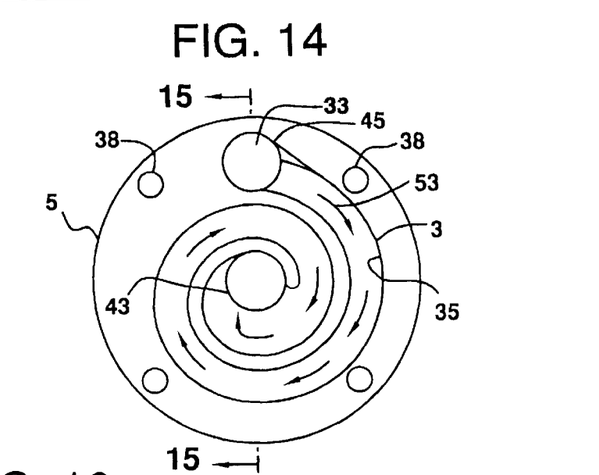
FIG. 14 is a front elevation of the groove plate.
Figure 15:
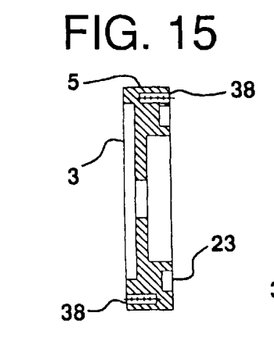
FIG. 15 is a cross section of the spiral groove plate of FIG. 14 at 15—15.
Figure 16:
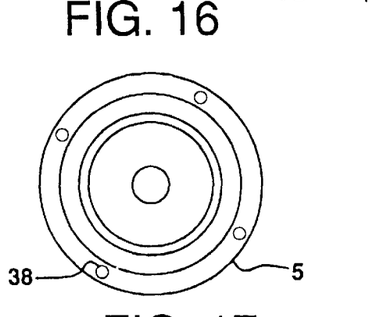
FIG. 16 is a rear view of a spiral groove plate.
Figure 25:
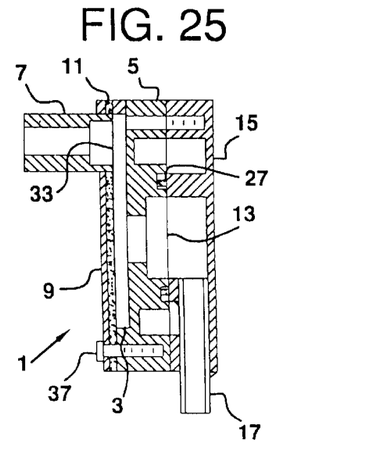
FIG. 25 is a cross-section of a SPIRAL SAMPLER like that of FIG. 1 but with a smaller filter.

The SPIRAL SAMPLER 1, shown in FIGS. 1, 2 and 25, is a sampler for airborne particles. A unique feature is a curved channel or spiral groove 3 in the groove plate 5. Air containing suspended particles enters the inlets of the front plate and the groove plate through the inlet tube 7, which is preferably attached at 90° to the front plate 9. Air leaving the inlet tube 7 turns sharply by 90° and enters the spiral groove 3 at its inlet 45 (FIG. 14).

The spiral groove 3 is a curved channel in the groove plate 5. The front plate 9 covers the channel, and a gasket 11 between the plates provides a vacuum seal.

Figures 3, 4, 5, 6, 7, 8, 9, 10, 11:
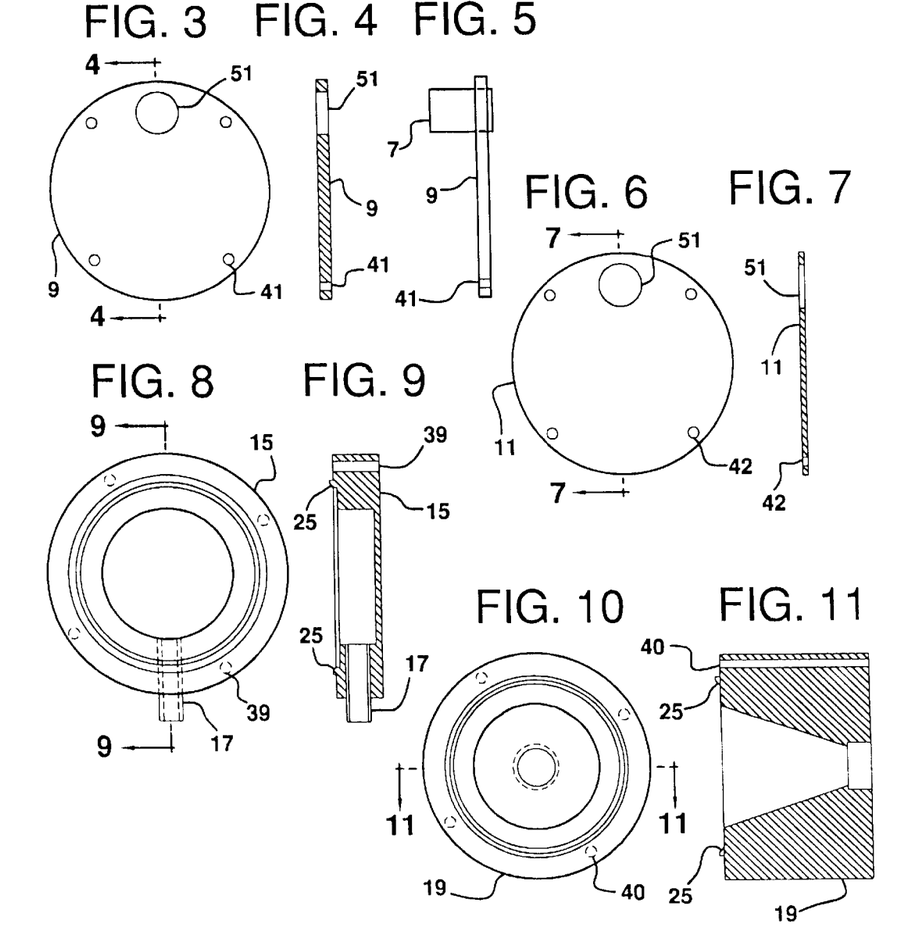
FIG. 3 is a front elevation of a front plate.
FIG. 4 is a cross-section of the front plate of FIG. 3 at 4—4.
FIG. 5 is a side elevation of a front plate.
FIG. 6 is a front view of a gasket between the spiral groove plate and the front plate.
FIG. 7 is a cross section of the gasket of FIG. 6 at 7—7.
FIG. 8 is a front elevation of a filter back plate.
FIG. 9 is a cross section of the filter back plate of FIG. 8 at 9—9.
FIG. 10 is a front elevation of an APS back plate.
FIG. 11 is a cross section of the APS back plate of FIG. 10 at 11—11.

FIGS. 3, 4 and 5 show front elevation, cross-section and side elevation views of the front plate 9, respectively. Fasteners 37 secure the front plate 9 and gasket 11 to the groove plate 5 through bolt holes 41, 42 and 38, respectively.

FIGS. 6 and 7 are front and cross sectional views of the gasket 11, respectively.

As seen in FIG. 1 (and FIG. 25), at the end 43 of the spiral groove 3, the air turns another 90° and exits the groove plate 5. The air then passes through a filter 13 held by the filter back plate 15, which is attached to the groove plate 5.

FIGS. 8 and 9 show front and cross-sectional elevation views of the filter back plate, respectively. Fasteners 47 in bolt holes 39 and 38 secure the filter back plate 15 to the spiral groove plate 5. Particles are deposited on the filter 13, shown in FIG. 1 (FIG. 25), which may be removed for analysis of particle mass and/or chemical composition.

Another preferred alternative is to replace the filter back plate 15 with the APS (Aerodynamic Particle Sizer) back plate 19, as shown in FIG. 2, to conduct the airborne particles to the entrance of an electronic particle detector, an existing device not part of this invention.

FIGS. 10 and 11 show front elevation and cross sectional views of an APS back plate 19. Fasteners 49 in bolt holes 40 and 38 secure the APS back plate 19 to the spiral groove plate 5. The particle detector counts and sizes the particles in real time. A number of other existing particle detectors may be used. The present invention may be used as a particle size selector at the inlet of other devices as well.

Figure 12A:
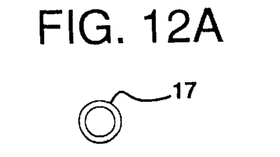
FIGS. 12A and 12B are front and side elevations, respectively, of an outlet tube.
Figure 12B:
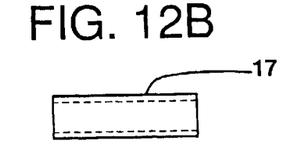

Air is drawn through the sampler by a vacuum pump attached to the outlet tube 17, FIGS. 12A and 12B, when the filter back plate 15 is used, or by the vacuum pump in the electronic particle detector when the APS back plate 19 is used.

Figure 13A:
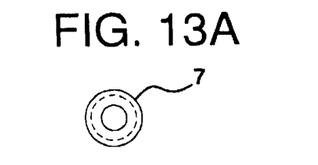
FIGS. 13A and 13B are front and side elevations, respectively, of an inlet tube.
Figure 13B:
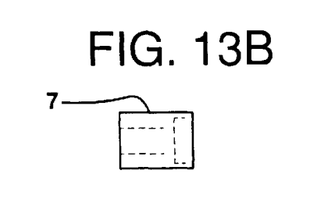

The inlet tube 7, detailed in FIGS. 13A and 13B, produces a jet of air that impinges on the surface 33 of the groove plate 5, shown in FIG. 14. That causes particles, considerably larger than those of interest, to impact on the surface 33 of the spiral groove plate 5.

Figure 17:
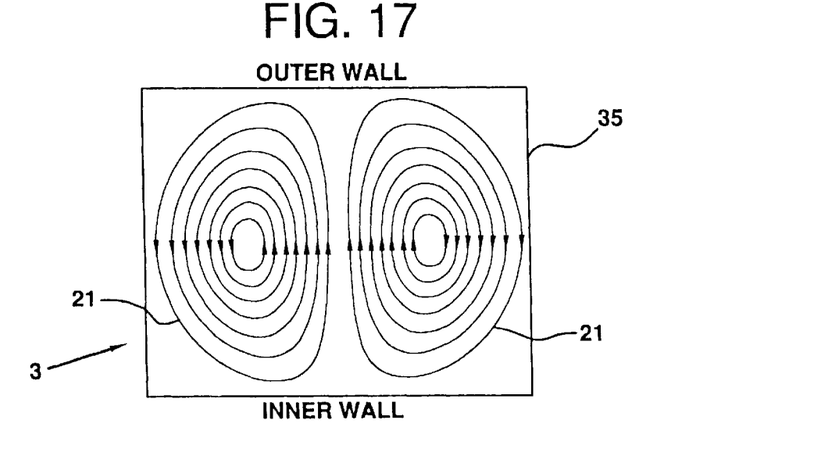
FIG. 17 is a schematic cross-section demonstrating secondary air circulation flow patterns within the groove and showing how particle deposition is enhanced by the secondary air flow.

Some particles are retained on the surface 33, others may bounce and enter the spiral groove 3 at its inlet 45 along with the smaller, suspended particles. The air flow 53 in the spiral groove 3 in FIG. 14 follows the curve of the groove, resulting in a centrifugal force toward the outside wall 35, as shown in FIGS. 14 and 17. That further results in the formation of two counter-rotating eddies 21. Thus, the overall air motion consists of two counter-rotating spirals 21 within the spiral groove 3. The secondary flows have a major effect in augmenting particle deposition on the outer walls 35 of the spiral groove 3. For given dimensions of the spiral groove and a given air flow rate, the percentage of particles penetrating to the filter (i.e., leaving the groove plate 5 at the end 43 of the spiral groove 3 without depositing) depends on the particle's aerodynamic diameter.

Figure 18:
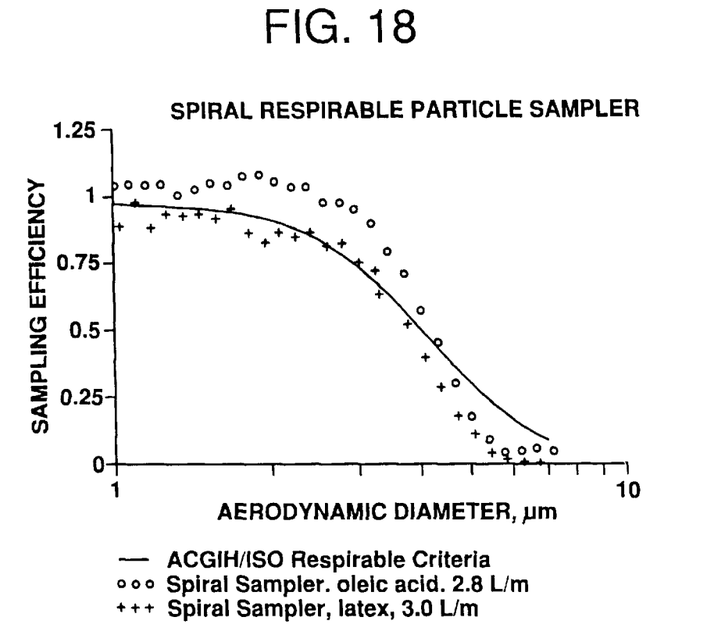
FIG. 18 is a graph showing sampling efficiency vs. particle size of the SPIRAL SAMPLER with the 4 µm groove plate for laboratory-generated aerosol of oleic acid particles and for latex particles.
Figure 19:
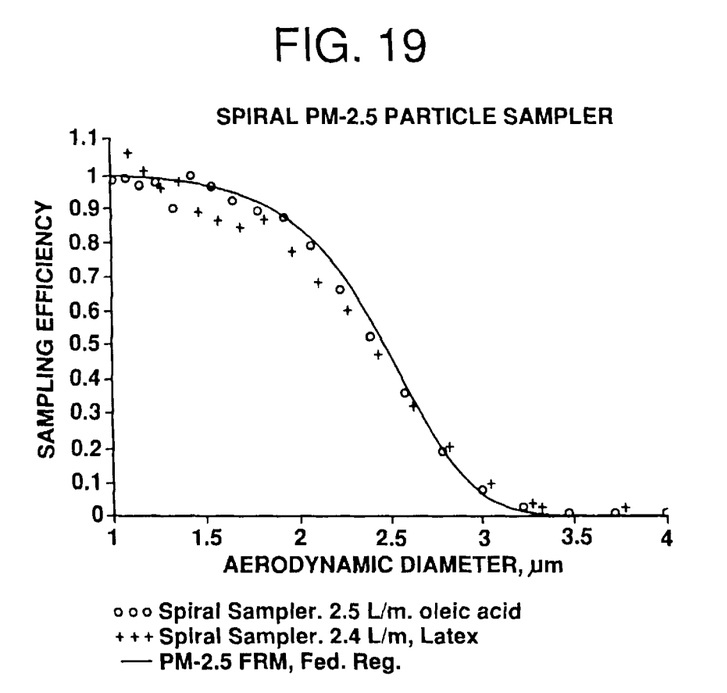
FIG. 19 is a graph showing sampling efficiency vs. particle size of the SPIRAL SAMPLER with the 2 µm groove plate for laboratory-generated aerosol of oleic acid particles and for latex particles.

The graph of percentage of particles penetrating vs. particle aerodynamic diameter will have a 50% efficiency (the cutpoint) and the curve will have a characteristic shape, as shown in FIGS. 18 and 19.

Three prototype SPIRAL SAMPLERS have been constructed and tested in the aerosol laboratory. One sampler, exemplified in FIGS. 18 and 20B, with the 4 $\mu$m groove plate, when operated at a flow rate of 2.8 liters/minute, has been shown to sample particles with a penetration curve closely following that of the ACGIH respirable mass criteria (American Conference of Governmental Industrial Hygienists).

Figure 20A:
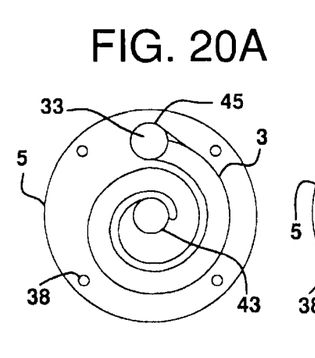
FIGS. 20A, 20B and 20C are respective front elevations of 6, 4 and 2.5 µm groove plates.
Figures 20B, 20C:
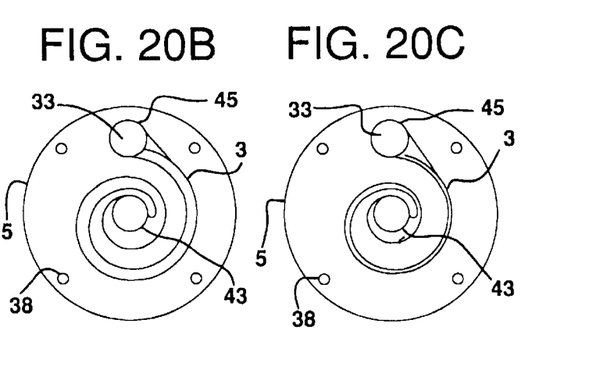

A prototype with the 2.5 $\mu$m groove plate, as for example in FIGS. 19 and 20C, when operated at a flow rate of 2.4 liters/minute, has been shown to sample particles with a penetration curve closely following that of the 1997 PM-2.5 Federal Reference Method for the sampling of ambient airborne particles by the U.S. Environmental Protection Agency.

A preferred sampler apparatus has a plate having an inlet and outlet. A curved channel connects the inlet and the outlet forming a flow path between the inlet and the outlet. The plate has front and rear walls. The front wall may include one or more openings for receiving fasteners. The rear wall may also include one or more openings for receiving fasteners.

One of the walls preferably has a groove. An O-ring is positioned in the groove. The O-ring is preferably of a rubber material. The plate may be of any material such as, but not limited to, aluminum, plastic and conducting plastic materials.

The utility of the sampler is in its ability to sample particles according to a desired penetration curve. An additional important requirement is that sticky or liquid particles and solid, or bouncy particles of the same aerodynamic diameter be sampled with the same efficiency. Testing of the prototype with particles of oleic acid, a liquid, and particles of latex, a solid, verify that the SPIRAL SAMPLER satisfies that requirement. The new design causes the particles to deposit relatively gently and at grazing angles on the walls, which inhibits solid particle bounce.

In addition, the particle deposition is distributed over a large area. Some existing particle samplers use oil or grease on the deposition surfaces to reduce particle bounce. However, that has the disadvantages that oil or grease may be dislodged and deposited on the filter. Also, vapors from the oil or grease may contaminate the particle deposit on the filter. The present SPIRAL SAMPLER is operated without oil or grease on the surfaces, thus eliminating the above disadvantages. A further advantage of the SPIRAL SAMPLER is the relatively small pressure drop because of the absence of any small orifices as in many other types of particle samplers.

By varying the dimensions of the inlet tube and the spiral groove as well as the number of turns of the spiral, a SPIRAL SAMPLER may be designed for sampling at any desired flow rate and with chosen particle size cutoffs. The SPIRAL SAMPLER may be made in a physically small version, such as the prototype, suitable for wearing on the person in combination with a small, battery-powered pump. The small, low flow rate version may also be used as a portable area sampler. Larger versions may be operated as area samplers with electrically-powered pumps.

The SPIRAL SAMPLER is a sampler for airborne particles. The spiral groove removes large particles from the air stream before it reaches the filter back 15, FIG. 1, or the APS back 19, FIG. 2, depending on which back is used.

Figure 21:
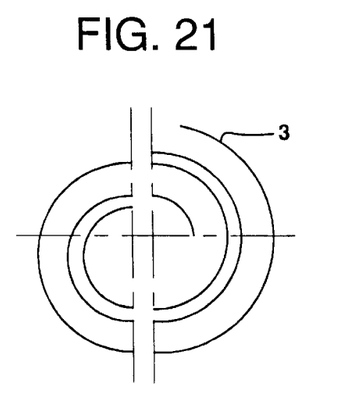
FIG. 21 is an elevation of the spiral groove.

Three different plates are specified, with different groove widths, but with the same groove depth, as for example, shown in FIGS. 20A, 20B and 20C. The spiral grooves may be formed from arcs of circles with various radii (see diagram of spiral groove, FIG. 21).

The critical tolerances are on the depth and width of the spiral grooves. Note that the absolute radii are not as important as the width of the groove. Also, the transitions between different radii are preferably smooth.

Figure 22:
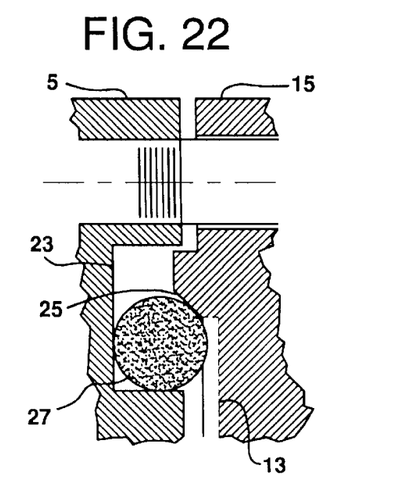
FIG. 22 is a detail of the O-ring between the spiral groove plate and the back plate.

The other critical tolerances are on the O-ring groove 23 and the beveled surfaces 25 of the filter back or APS back. As shown in FIG. 22. Note that the O-ring groove 23 is not conventional. The O-ring 27 fits the inner diameter of the O-ring groove 23. On the outside, the O-ring 27 seals against the beveled edge 25 on the opposing surface, i.e., the filter or APS back. This configuration seals against the filter and also against the outside. For this configuration to be effective, the dimensions must be accurate.

All parts are preferably of aluminum, plastic or conducting plastic except for the O-ring and the gasket, which are rubber.

The SPIRAL SAMPLER is an instrument to be used in the general field of air pollution, in particular, the sampling of airborne particulate matter for the measurement of the concentration and/or the determination of the chemical composition of the particles. Such airborne particles may be located in the outside air where concentration measurements are needed by governmental agencies seeking to protect the public health. Airborne particles are also found indoors and in workplaces, where industrial hygienists assess and control health hazards.

The invention provides a sample of airborne particles according to a prescribed sampling convention such as the ACGIH Respirable Particle Mass or the U.S. Environmental Protection Agency's PM 2.5. The sampler is capable of collecting particles of a given aerodynamic diameter with the same efficiency, whether they are sticky or bouncy, and without having greased or oiled surfaces. The sampler is more compact than the most widely used current personal samplers. It may be mass-produced economically because of the relatively simple configuration. Because the assessment of airborne particle pollution is necessary in the outdoors, in workplaces and indoor areas, just about everywhere, the potential market is very large.

The new size-selective aerosol particle sampler samples particles below a given particle aerodynamic range. The size selection is made by the new particle size selection device. Particles enter the inlet opening and turn 90° thereby causing the largest particles to impact on the back wall. The remaining particles travel around in the spiral groove. Centrifugal force causes larger particles to deposit on the outer wall of the groove. Smaller particles remain airborne and exit to a filter collector or a particle sensor. The 50% particle size cut-off and the shape of the cut-off curve are determined by the airflow rate, the size of the groove and the length or number of turns of the groove.

Figure 23:
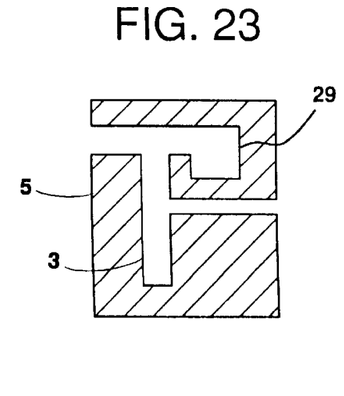
FIG. 23 is a cross-section schematically showing a particle trap opposite the inlet.

A particle trap 29, as shown in FIG. 23, may provide a removal mechanism for loadings of large particles. The trap 29 may be a virtual impaction stage, removing particles larger than a given size.

Figure 24:
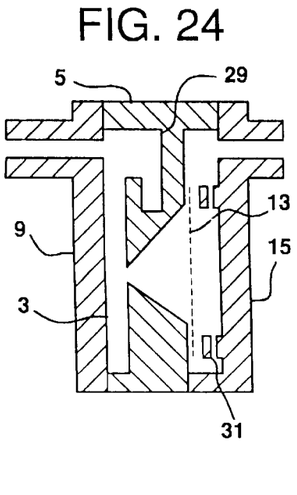
FIG. 24 is a cross-section schematic showing a new filter sampler.

A conceptual design for a filter sampler is shown on the filter sampler schematic drawing, FIG. 24. The front plate 9 may be removed to clean the spiral groove 3 and particle trap 29. The front plate 9 is backed by a flat gasket to seal the spiral groove 3. In the filter sampler, the back plate 15 may be removed to change the filter 13. The filter 13 is held in place by filter supports 31. A particle sensor may replace the filter. In both cases, the new SPIRAL SAMPLER effectively and compactly separates the oversized particles that otherwise would adversely affect the sampling.

As seen in FIG. 25, filter size may be varied as needed.

The spiral groove sampler provides aerodynamic particle size selection. Particle size cut-off may be selected over a wide inertial size range. The new sampler may be scaled to any size from personal to area sampler. The flat geometry enables the design of a badge-type personal sampler. It may be used with a pocket pump or a belt-type pump. The design is tolerant of high loadings and coarse particles. The new sampler is simple and low cost for manufacturing. It may be replicated by automated mills or by plastic molding. The new sampler may be designed for low or high flow rates.

While the invention has been described with reference to specific embodiments, modifications and variations of the invention may be constructed without departing from the scope of the invention, which is defined in the following claims.

I claim:

1. A sampler apparatus comprising a spiral groove plate, a front plate and a backing plate;

first and second walls on the spiral groove plate;

a first inlet in the first wall, a first outlet in the second wall and a spiral groove connecting the inlet and outlet forming a flow path between the inlet and outlet;

third and fourth walls on the front plate;

a second inlet in the third wall and a second outlet in the fourth wall, wherein the second outlet of the front plate connects to the first inlet of the spiral groove plate;

fifth and sixth walls on the backing plate;

a third inlet in the fifth wall and a third outlet in the sixth wall, wherein the third inlet of the backing plate connects to the first outlet of the spiral groove plate; and wherein the spiral groove comprises transitions of arcs of circles having decreasing radii.

2. The apparatus of claim 1, further comprising a filter support connected to the second wall and a filter mounted between the second wall and the filter support.

3. The apparatus of claim 1, further comprising an airborne particle sizer back plate connected to the second wall for conducting airborne particles to an entrance of an electronic particle detector.

4. The apparatus of claim 1, further comprising a particle trap connected to the inlet for collecting large particles.

5. The apparatus of claim 1, further comprising a backing plate connected to the second wall, the second wall and the backing plate forming a cavity, a projection surrounding an enclosure extending from the backing plate to the rear wall, a filter mounted between the projection and the rear wall, and a passage in the rear wall for gas passing through the filter.

6. The apparatus of claim 1, further comprising a filter between the backing plate and the spiral groove plate.

7. The apparatus of claim 1, further comprising a recess in the fifth wall of the backing plate for receiving and positioning the filter in the flow path.

8. The apparatus of claim 6, further comprising a screen for receiving the filter.

9. The apparatus of claim 1, wherein the first wall of the spiral groove plate further comprises at least one opening for receiving fasteners.

10. The apparatus of claim 1, wherein the second wall of the spiral groove plate further comprises at least one opening for receiving fasteners.

11. The apparatus of claim 1, further comprising a groove in the second wall of the spiral groove plate.

12. The apparatus of claim 11, further comprising an O-ring in the groove in the second wall of the spiral groove plate.

13. The apparatus of claim 12, wherein the O-ring is of a rubber material.

14. The apparatus of claim 12, wherein the fifth wall of the backing plate further comprises a beveled surface for holding the O-ring in the groove in the second wall of the spiral groove plate in an assembled sampler.

15. The apparatus of claim 1, further comprising at least one opening in the front plate, and complementary openings in the first wall of the spiral groove plate, and fasteners provided in the openings for securing the front plate to the spiral groove plate.

16. The apparatus of claim 1, further comprising at least one opening in the backing plate, and complementary openings in the second wall of the spiral groove plate, fasteners provided in the openings for securing the backing plate to the spiral groove plate.

17. The apparatus of claim 1, wherein the spiral groove plate is of an aluminum material.

18. The apparatus of claim 1, wherein the front plate is of an aluminum material.

19. The apparatus of claim 1, wherein the front plate is of a conducting plastic material.

20. The apparatus of claim 1, wherein the backing plate is of an aluminum material.

21. The apparatus of claim 1, wherein the backing plate is of a conducting plastic material.

22. The apparatus of claim 1, further comprising a gasket positioned between the front plate and the spiral groove plate.

23. The apparatus of claim 22, wherein the gasket is of a rubber material.

24. The apparatus of claim 1, further comprising an inlet tube in the second inlet in the third wall of the front plate.

25. The apparatus of claim 1, further comprising a third opening in the sixth wall of the backing plate communicable with and conducting flow to another sampler.

26. The apparatus of claim 1, wherein the sixth wall is a side wall of the backing plate and wherein the third outlet is in the side wall.

27. The apparatus of claim 1, wherein the sixth wall is a rear wall of the backing plate and wherein the third outlet is in the rear wall.

28. A method for sampling comprising providing a spiral groove plate with transitions of arcs of circles having decreasing radii, the spiral groove plate having a first and a second wall, connecting a front plate to the first wall of the spiral groove plate, and connecting a backing plate to the second wall of the spiral groove plate, supplying a sample to the spiral groove plate, passing the sample through the spiral groove plate, receiving the sample passed through the spiral groove plate, collecting particles from the sample exiting the spiral groove plate and analyzing the collected particles.

29. The method of claim 28, further comprising a third opening in the sixth wall of the backing plate communicable with and conducting flow to another sampler.

30. The method of claim 28, further comprising providing a filter between the second wall and the backing plate for collecting particles.

31. The method of claim 28, further comprising providing a gasket between the front plate and the spiral groove plate for providing a vacuum seal.

32. The method of claim 28, further comprising providing a groove in the second wall of the spiral groove plate.

33. The method of claim 32, further comprising providing an O-ring in the groove in the second wall of the spiral groove plate for creating a tight seal between the spiral groove plate and the backing plate.

34. The method of claim 28, wherein providing the spiral groove plate comprises providing a first inlet in the first wall, a first outlet in the second wall, and connecting the first inlet and the first outlet by a spiral groove.

35. The method of claim 34, further comprising varying the dimensions and number of turns of the spiral groove for sampling at any flow rate and for predetermining particle size cutoff.

36. The method of claim 34, wherein providing the front plate comprises providing a second inlet in the front plate complementary to the first inlet in the first wall of the spiral groove plate.

37. The method of claim 36, further comprising providing an inlet tube in the second inlet of the front plate.

38. The method of claim 37, further comprising varying the dimensions of the inlet tube for sampling at any flow rate and for determining particle size cutoff at an entrance to the spiral groove.

39. The method of claim 34, wherein providing the backing plate comprises providing a third inlet in the backing plate complementary to the first outlet in the second wall of the spiral groove plate.

40. The method of claim 28, further comprising providing a filter in a cavity between the second wall and the backing plate.

* * * * *